United States Patent [19]

Imagawa et al.

[11] Patent Number: 4,474,877
[45] Date of Patent: Oct. 2, 1984

[54] PROCESS FOR DETECTION AND MEASUREMENT OF VIRAL SPECIFIC IMMUNOGLOBULINS AND ARTICLE OF MANUFACTURE THEREFOR

[75] Inventors: David T. Imagawa, Rancho Palos Verdes; Hong D. Bui, Cerritos, both of Calif.

[73] Assignee: Research and Education Institute, Inc. Harbor - UCLA Medical Center, Torrance, Calif.

[21] Appl. No.: 188,815

[22] Filed: Sep. 19, 1980

[51] Int. Cl.$^3$ .................... C12Q 1/70; G01N 33/54
[52] U.S. Cl. ............................................ 435/5; 435/7; 435/810; 436/513; 436/528; 436/531; 436/532; 436/808
[58] Field of Search ................. 435/5, 7, 8, 235, 239, 435/240, 241, 810; 23/230 B; 424/1, 1.5, 12; 436/528, 531, 532, 808, 513

[56] References Cited

U.S. PATENT DOCUMENTS

| | | | |
|---|---|---|---|
| 3,553,310 | 1/1971 | Csizma et al. | 424/2 |
| 4,016,043 | 4/1977 | Schuurs et al. | 435/5 |
| 4,024,020 | 5/1977 | Weiss et al. | 435/240 |
| 4,024,235 | 5/1977 | Weetall | 435/5 |
| 4,036,693 | 7/1977 | Levine et al. | 435/241 |
| 4,040,905 | 8/1977 | Petricciani et al. | 435/5 |
| 4,189,464 | 2/1980 | Blumberg et al. | 424/1 |
| 4,210,723 | 7/1980 | Doorman et al. | 435/7 |
| 4,266,032 | 5/1981 | Miller et al. | 435/241 |
| 4,267,270 | 5/1981 | Stout | 435/7 |
| 4,273,756 | 6/1981 | Ling et al. | 424/1 |

OTHER PUBLICATIONS

Kalimo et al., "Solid-Phase Radioimmunoassay of Human Immunoglobulin M and Immunoglobulin G Antibodies Against Herpes Simplex Virus Type 1, Capsid, Envelope and Excreted Antigens, *Infection & Immunity*, vol. 15, No. 3, (1977), pp. 883-889.
Kalimo et al., "Solid-Phase Radioimmunoassay of Herpes Simplex Virus IgG and IgM Antibodies", *J. Immun. Meth.*, (1977), pp. 183-195.
Kalimo, "Solid-Phase Radioimmunoassay of Antiviral IgG and IgM Class Antibodies", Turku, (1977).
Wezel, "Growth of Cell-Strains and Primary Cells on Micro-Carriers in Homogeneous Culture", *Nature*, vol. 216, (1967), pp.64-65.
Kalimo et al., "Solid-Phase Radioimmunoassay of Rubella Virus Immunoglobulin G and Immunoglobulin M Antibodies", *J. Cin. Microbiol.*, vol. 4, No. 2, (1976), pp. 117-123.
Arstila, et al., "A Solid-Phase Radioimmunoassay for IgG and IgM Antibodies Against Measles Virus", *J. Gen. Virol.*, vol. 34, (1977), pp. 167-176.

*Primary Examiner*—Thomas G. Wiseman
*Attorney, Agent, or Firm*—I. Morley Drucker

[57] ABSTRACT

This invention relates a simplified and reliable process for the detection and measurement of viral specific immunoglobulins such as IgG, IgM and IgE wherein relatively large-diameter plastic beads, e.g., $\frac{1}{4}''$, diameter polystyrene balls with a specular finish, are used as the solid matrix upon which a high concentration of standard cells are first grown or cultured. The cells are then infected with a particular virus to express a high concentration of unpurified viral antigen(s), and are then fixed to preserve the viral antigen(s) concentration. The resulting fixed plastic beads (PB) are washed (to remove fixing agent) and then employed as the basis of the detection of specific immunoglobulins in the patient's serum. The detection process involves simply incubating a measured dilution of patient serum with each PB whereby the various specific immunoglobulins in the patient serum will attach to the viral antigen(s) on the PB. The specific immunoglobulins (e.g. IgG) desired to be measured is detected by the addition, to the PB container, of the anti-human specific immunoglobulin (e.g., anti-human IgG) in tagged format, e.g., in radioactive form. The tagged anti-human specific immunoglobulin binds to the specific immunoglobulin and by measuring the amount of the tagged anti-human specific anti-globulin, one obtains a direct measurement of the amount of the desired specific immunoglobulin present in the patient serum.

The process techniques offer the advantages of easy preparation, storage and handling of the basic unit (PB) used for measurement, and offers increased sensitivity and substantial savings in assay time over prior art methods.

8 Claims, 2 Drawing Figures

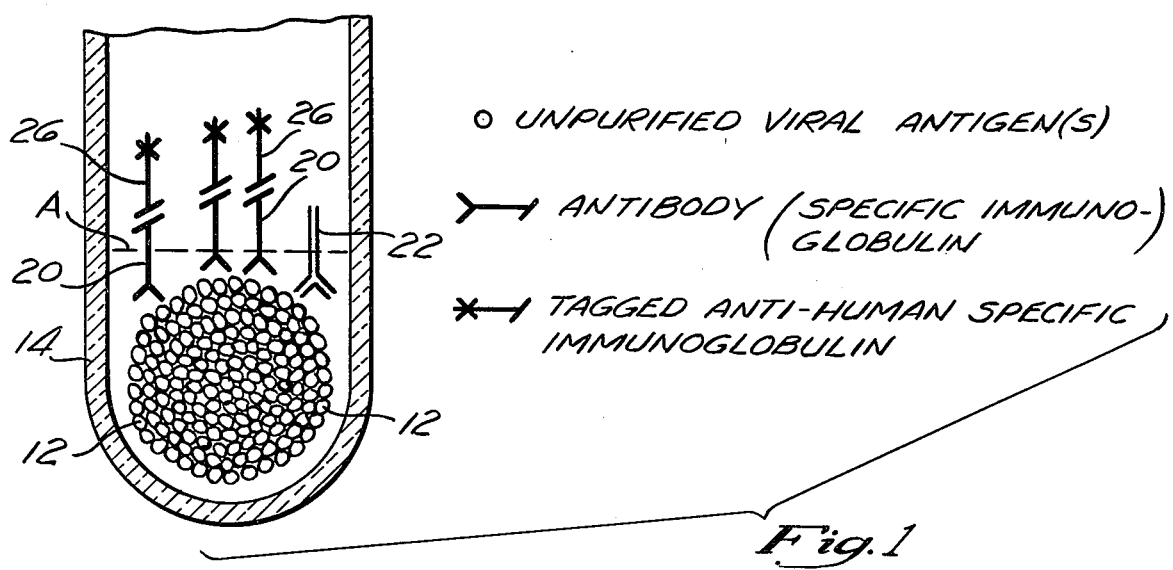
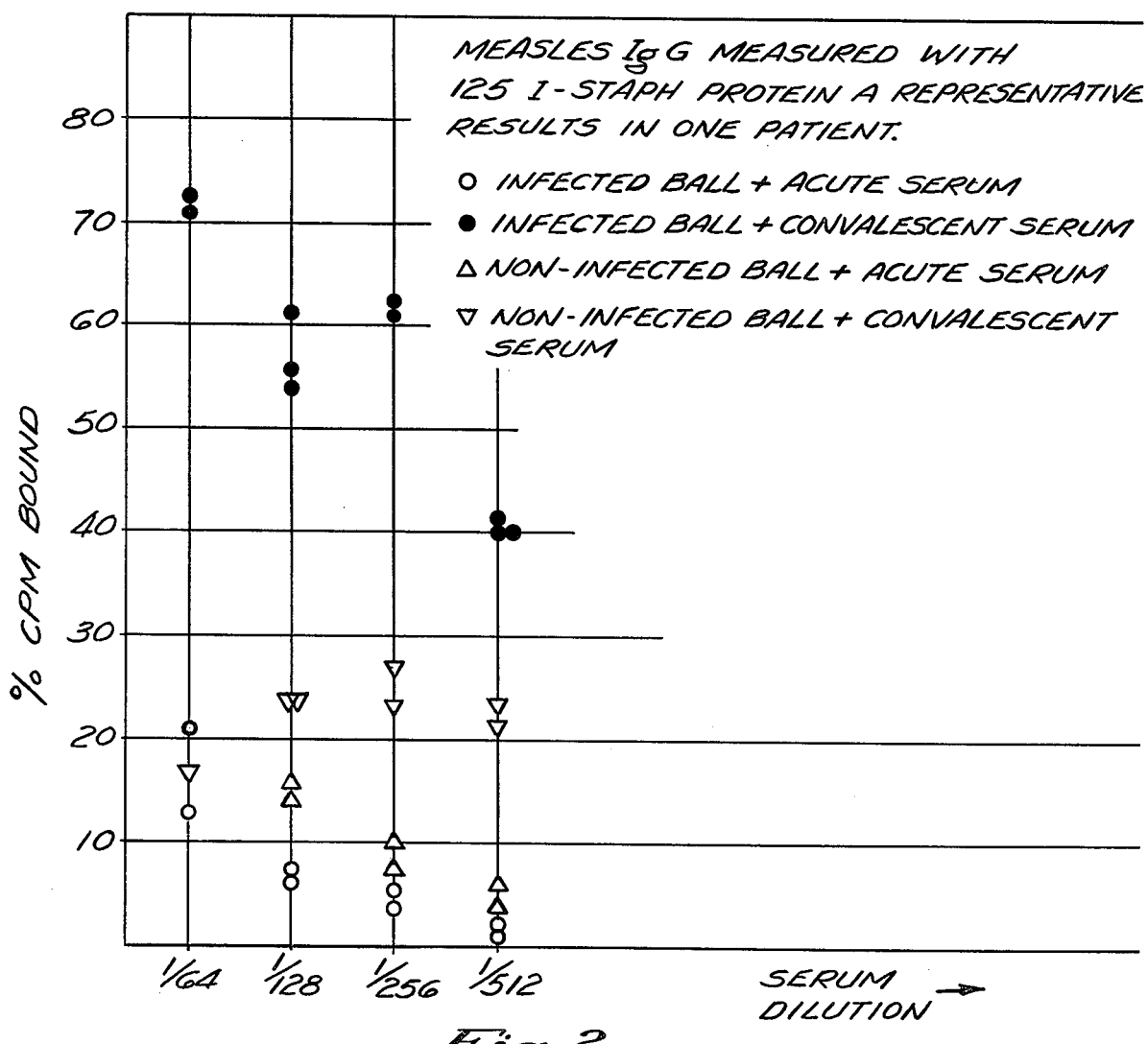

PROCESS FOR DETECTION AND MEASUREMENT OF VIRAL SPECIFIC IMMUNOGLOBULINS AND ARTICLE OF MANUFACTURE THEREFOR

This invention was partially supported by a grant from the National Institute of Allergy and Infectious Diseases (National Institute of Health), Grant No. 5-T32 AI07014-04.

BACKGROUND OF THE INVENTION

1. Field of the Invention

This invention relates to a diagnostic method for the detection and measurement of viral specific immunoglobulins in animals or humans utilizing relatively large diametered solid-phase carrier units or balls as the basic unit upon which the immunologic reactions occur.

2. Prior Art

The use of solid phase carriers for detection and measurement of viral specific immunoglobulins is well known. Thus, large diametered (e.g. ¼" diameter) polystyrene balls have been used as a carrier for *purified* viral antigens following which viral specific immunoglobulins are attached to the purified antigen and detected by RIA or other tracer methods. Such techniques are set forth in detail in the following prior art:

(1) K. Kalimo, *Solid-Phase RIA of Rubella Virus IgG and IgM Antibodies*—J. Clin. Microbiol. (August, 1976), pages 117–123;

(2) K. Kalimo, *Solid-Phase RIA of Human IgM and IgG Antibodies Against Herpes etc.*—Infec. Immunity, (March, 1977), pages 883–889;

(3) P. Arstila, *A Solid-Phase RIA for IgG and IgM Antibodies Against Measles Virus*—J. Gen. Virol., (1977), pages 34, 167–176;

(4) K. Kalimo, *Solid-Phase RIA of Herpes Simplex IgG and IgM Antibodies*—J. Immunol. Methods, 14 (1977), pages 183–195; and (5) K. Kalimo, *Solid-Phase RIA of Antiviral IgG and IgM Class Antibodies* (Thesis, 1977) U. of Turku—Dept. of Virology—SF 20520—Turku, Finland.

There are substantial drawbacks, however, in making purified viral antigens; and furthermore generally only a single purified antigen is absorbed or coated onto the ball. In contrast, the process of this invention utilizes large-diametered plastic balls of the type heretofore employed, but utilizes them, in a different fashion, to permit the expression of most, if not all, of the antigens of the particular virus on a single large-diametered ball.

Large diameter polystyrene balls have also been coated with an antibody for detection of a specific antigen (AUSRIA II-125 ®, Abbott Laboratories, North Chicago, Ill.). The AUSRIA methodology does not contemplate the expression of unpurified viral antigen(s) on the polystyrene ball.

The prior art also teaches the production and use of unpurified viral antigens on *microcellular* structures for the purpose of vaccine production and the like (*Nature*, Vol. 216 (Oct. 7, 1967), A. L. Van Wezel; and *Technical Information*, "Microcarrier Cell Culture with Cytodex TM 1",Pharmacia Fine Chemicals (Piscataway, N.J.) ). The use of microcarriers carrying unpurified viral antigens for the detection of specific immunoglobulins has substantial drawbacks as well. The process of measurement is time-consuming in that a great number of washing and centrifuging steps must be performed in order to retain the microcarriers and their absorbed specific immunoglobulins for measurement. And because of the washing steps required, one also does lose a significant amount of microcarriers, and their absorbed viral antigen, thus reducing the viral antigen concentration perhaps by a significant amount.

In short, solid phase detection and measurement of viral specific immunoglobulins has been hampered by lack of simple techniques. In the closest prior art known of (Kalimo, supra) viral antigen concentration and purification are major difficult and time-consuming steps. The solid phase assay described herein offers a simple method of viral antigen preparation for specific immunoglobulins detection with advantages: easy preparation, storage and handling, increased sensivity of assays due to increased concentration of stable antigens, and the potential of quantitative assessment of specific antibody response in recent primary infection of pregnant women, newborns, vaccinees, etc.

BRIEF SUMMARY OF THE INVENTION

A solid phase assay has been designed to detect viral specific immunoglobulins utilizing plastic spheres or balls of a sufficiently large size and weight that they can be easily handled and stored; they are visible without the aid of microscopes or other magnification equipment and need not be separated from liquid medium by centrifugation. Such balls are preferably made of polystyrene, have a specular finish and preferably have a diameter of between about 4–8 mm.

Standard cells that are readily grown, e.g., Hep 2 or Vero cells, or normal diploid cells are grown on the plastic balls (PB) and infected with a particular virus of a single class, e.g., measles virus (MV) or rubella virus (RV), the specific immunoglobulin to which is to be detected.

The infected cells are then fixed, by standard fixing agents and methods, to preserve the unpurified viral antigen(s) expressed by the infected cells and essentially completely maintain the concentration of the viral antigen(s).

After blocking free binding sites on the PB by washing with, e.g., Human Serum Albumin in phosphate buffer, each PB is then incubated with a dilution of negative control serum, or serum from a patient who has suspected infection with the virus with which the PB was originally infected (e.g., MV or RV). The PB's are then washed to remove the non-attached antibodies. At this point, the PB carries a high concentration of viral antigen(s) combined with specific immunoglobulins attached to the antigen(s).

The specific immunoglobulin on the PB may now be readily detected by the incubation of the appropriate tagged anti-human immunoglobulins or proteins which bind specifically with immunoglobulins. Thus, for example, $^{125}I$-rabbit anti-human IgM or $^{125}I$-Staph. protein A is incubated with PB, the excess tagged component washed off, and specifically bound IgG or IgM is detected by standard RIA methods. Other non-radioactive tagging media and methods may also be employed.

By way of example, using the method and PB of this invention with RIA techniques, significant binding of specific IgG to MV infected PB was obtained with serum taken from a patient with MV in the convalescent stage as contrasted with a very low binding with acute and control sera.

Assay of cerebrospinal fluid (CSF) may also be performed for viral specific immunoglobulins following the process steps of this invention.

The use of this novel method, employing relatively large sized plastic spherical balls as solid phase carriers for infected cells to express viral antigen(s) has the advantages of increased simplicity, sensitivity and reliability and economy.

It will be seen that the polystyrene or other plastic balls employed herein for detection of viral specific immunoglobulins are each provided with a high concentration of stable viral antigen(s). A kit, employing a plurality of such polystyrene balls each contained in its own test well, test tube or other container, with or without tagging components, and other chemicals, and control PB's also lies within the scope of this invention. Such a kit form could be used to readily process large numbers of patient sera and control sera.

BRIEF DESCRIPTION OF THE DRAWINGS

FIG. 1 is a schematic representation of the solid phase carrier of this invention, at an intermediate point in the process of this invention; and FIG. 2 is a graphical representation of the concentration of measles IgG in various patient and control sera.

DETAILED DESCRIPTION OF THE INVENTION

The presently preferred process for detecting viral specific immunoglobulins comprises the following method and means:

I. Preparation of Polystyrene Balls

1. Polystyrene balls of 6.5 mm diameter, having a specular finish (manufactured by Precision Plastic Ball Co. of Chicago, Ill. 60641) are used as the solid phase carrier for the growth of cells and subsequent production of viral antigen(s). Other plastic balls varying in diameter from between about 4–8 mm may be also employed, the chief parameters being that each solid phase carrier should be of a size and weight sufficiently great to be separable from a liquid medium (e.g., an aqueous washing medium or patient serum) without centrifugation. Also, the size of the plastic ball (PB) should be such that sufficient number of cells may be grown to express a sufficient amount of viral antigen(s) to measure the expected highest titre of viral specific immunoglobulins in the patient sera. It is believed that somewhere between 200,000–500,000 cells/PB are presently preferred to be grown to thereafter express the proper number of viral antigen(s).

By way of example, Hep 2 or Vero cells were grown on polystyrene balls of ¼" diameter (Precision Plastic Ball Co., Chicago, Ill.)—the concentration of such cells being between 2 and $4 \times 10^5$ cells/ball.

Many other types of cells may be grown on the polystyrene balls, the particular types of cell chosen being that in which the virus required can be most readily grown and viral antigen(s) expressed.

2. After the cells have been grown on PB, under standard conditions such as those set forth in any one of a number of cell culture textbooks, the cells are infected with a virus of a single class, for example Edmonston measles virus (MV) or clinical isolate of rubella virus (RV). The conditions under which the cells are infected are conventional in the art, viz: Stock viruses are added to cell cultures and allowed to replicate under appropriate conditions, e.g., at 36°–38° C. for a given number of days depending upon the virus. Measles infection is observed by the development of syncytia and the presence of virus in the media. Rubella infection is identified by challenge of infected balls with ECHO II virus. This is a standard method employed for detection of rubella virus replication. The cells/PB are quantitated by selecting two balls from each batch and having them undergo standard cell-counting techniques such as by the use of trypsinization techniques.

3. The PB's carrying the infected cells are then fixed, with conventional fixing agents such as a 1% solution of glutaraldehyde. The fixing agent will destroy the virus infectiousness but preserves, essentially completely, the amount or concentration of viral antigen(s) that has been produced by the infected cells.

4. Cells were grown on polystyrene balls as set forth in Step 1 but the cells were not infected. These balls were used as control antigen, and care was taken to prepare a similar number of cells on the non-infected ball as on the infected ball.

5. After fixation of both the control and infected PB's, in the manner set forth in Step 3 above, the PB's were washed three times with a solution of phosphate buffer saline (PBS) to essentially remove the fixing agent from the PB's.

The control PB's and the infected PB's form the basic units of the detection procedure, and it is to be understood that each of these basic PB units can be placed in its own test tube, test well or other test container, and employed for the detection of virus specific immunoglobulins in a large number of patient sera.

II. Detection Procedure

1. In commencing the detection procedure, the viral antigen(s), and control, PB's are first chemically treated so as to prevent a false positive reaction with respect to the anti-human specific immunoglobulin being employed as the tagging medium. Thus, for example, if a radioactive tag is to be used for detection, the viral antigen(s), and control, balls are absorbed for 4–6 hours with 5% Human Serum Albumin in phosphate buffer (HSA) in order to prevent the free binding sites on the PB's from binding to the radioactive anti-human specific immunoglobulin.

2. The HSA solution is removed from the PB's with three separate PBS washes. 3. Patient sera, buffer solution or control sera are then incubated with the negative control and viral antigen balls as follows:

Serial dilutions of sera from patients (e.g., with measles or rubella) are first prepared in HSA. Diluted sera or buffer are added to tubes containing the viral antigen and control PB's at a volume of 200μper tube. Triplicate determinations for each of the patient sera and negative control sera are preferably made.

Incubation was performed at room temperature, on a shaker, with tubes in upright position, for a period of 4–6 hours.

Three saline washes are then performed to wash off unattached antibodies.

4. Incubation of the PB's with tagged anti-human specific immunoglobulin or other protein specific immunoglobulin now proceeds. In this connection, tracers or tags for the anti-human specific immunoglobuins may be non-radioactive as well as of the radioactive type. For example, an enzyme trace system such as enzyme linked immunoabsorbent assay (ELISA) may be employed, in which the tracer or tag measured, spectrophotometrically, is the amount of reaction caused by the enzyme bound to the viral antigen. Fluorescent dye tags or tracers may also be attached to anti-human specific immunoglobulins and then incubated with PB's of this invention. The amount of fluorescence detected determines the extent of the presence of the specific immunoglobulin bound to the PB's.

By way of a specific example, $^{125}$I-Staphylococcal protein A (Staph. protein A, Pharmacia Fine Chemicals) or $^{125}$I-Goat anti-human immunoglobulins G or M (Goat antihuman IgG and IgM, antibody incorporated and bionetics) were added at a total initial count of 100,000 cpm (counts per minute) per tube, and incubated with the PB at room temperature, on a shaker, for 4–6 hours. Excess tagged reagent was removed by a series of saline washes.

A Littman Gamma counter was employed for counting of radioactivity. The percent bindings were calculated and corrected by substraction of background given by antigen and control antigen balls incubated with HSA buffer.

A schematic representation of the methodology means employed in this invention is set forth in FIG. 1 of the drawings. The PB 12 is shown, within a test tube 14, the unpurified viral antigen 16 being depicted as essentially covering the surface of the PB. Patient sera has been added to the test tube 14 to the level shown by the dotted line A, which level is sufficient to completely cover the PB.

The patient sera, in FIG. 1, is illustrated as having at least two different varieties of specific immunoglobulins 20, 22, which may be, for example, IgG and IgM respectively. These various specific immunoglobulins bind to the available binding sites on the unpurified viral antigen(s).

Tagged anti-human specific immunoglobulins 26 (the specific immunoglobulin of which is to be detected , e.g., anti-human IgG) then binds only to the specific immunoglobulin (e.g., IgG) on the PB. The tagged anti-human specific immunoglobulin is then measured by known techniques, as earlier set forth, and this measurement gives a direct correlation to the amount of the specific immunoglobulin (e.g., IgG) in the patient sera.

Referring to FIG. 2 of the drawings, results are shown graphically for the detection of specifically bound IgG and IgM in various patient sera and control sera by means of the just described methodology and means utilizing the RIA techniques set forth above. It will be noted, in FIG. 2, that significant binding of specific IgG to MV infected PB was obtained with convalescent MV serum, 40.7%±0.2 (mean±SEM) compared to 4.5%±0.3 and 4.2% with the acute and control sera all diluted 1/512.

The following tabulation shows the results of IgM binding onto the PB's in accordance with the teachings of the invention, as aforesaid.

| RUBELLA IgG AND IgM: RESULTS OF ONE PATIENT (HI TITERS: ACUTE < 1/10, CONVALESCENT 1/640) | | |
|---|---|---|
| SERUM DILUTION | CPM BOUND MEAN ± SEM | % BOUND MEAN ± SEM |
| RUBELLA SPECIFIC IgG | | |
| NEGATIVE CONTROL 1/64 | 3306 ± 8 | 8.2 ± 0.1 |
| ACUTE 1/64 | 3496 ± 322 | 8.6 ± 0.8 |
| CONVALESCENT 1/64 | 5982 ± 1544 | 13.4 ± 3.8 |
| RUBELLA SPECIFIC IgM | | |
| NEGATIVE CONTROL 1/32 | 7300 ± 556 | 4.8 ± 0.4 |
| ACUTE 1/32 | 28984 ± 4486 | 19.2 ± 2.6 |
| CONVALESCENT 1/32 | 28208 ± 2341 | 18.7 ± 1.5 |

It will be seen that MV infected PB showed higher binding of IgG in rubella convalescent serum (13.4%±3.8) than in acute (8.7%±0.8) or control (8.2%±0.1). IgM binding in a pair of acute (19.2%±2.6) and convalescent (18.7%±1.5) rubella sera drawn two weeks apart was significantly higher than that of an uninfected control (4.8%±0.4).

The polystyrene ball method for solid phase radioimmunoassay offers many advantages including: easy preparation and storage of a large number of solid phase carriers of viral antigens, and solid phase control carriers, convenient handling of the PB carriers through washing steps, the ability to grow a large number of cells on the PB ($2 \times 10^5$ to $4 \times 10^5$ cells per ball) which increases the sensitivity of assays due to increased concentration of viral antigens, the quantitative assessment of specific antibody response in primary viral infections, and the use of the enzyme linked immunosorbent assay (ELISA) system.

In addition, a number of the solid phase carriers of viral antigens and the control antigens may be readily employed in a kit form by placing each PB in a separate test tube, or test well, and conducting the detection process steps using said kit format.

The kit of this invention takes the form of a plurality of test cavities with one solid phase carrier (PB) being placed in each of the test cavities (e.g., the test cavity could be a test well or test tube). At least some of the PB's would be infected cell PB's with a substantial concentration of unpurified viral antigen(s) and the remainder would be non-infected PB's. The non-infected PB's would have a zero to insignificant amount of viral antigen expressed thereon.

A variation of the procedure set forth herein may also be employed to detect and identify unknown viral antigen. In this case, one will infect the cells grown on the PB with the unknown viral antigen, fix the antigen, and detect and identify the antigen by incubating the unknown antigen PB with a series of specific immunoglobulins, in sequence, measuring the type and amount of binding by standard techniques and thereby determining the identity and extent of the antigen present.

Other modifications will be apparent to those skilled in the art. Hence, we intend to be bound only by the claims which follows:

We claim:

1. A process for detecting viral specific immunoglobulins in a fluid, which comprises:
    growing cells on a polymeric solid phase carrier of a size and weight sufficiently great to be separable from an aqueous medium without centrifugation;
    infecting the cells, grown on said polymeric solid phase carrier, with a particular virus of a single class to produce unpurified viral antigen (s) therein;
    immobilizing the said infected cells with a fixing agent of the type which destroys the viral infectiousness of said infected cells, but which preserves essentially completely, the concentration of said unpurified viral antigen(s) at the level at which it was initially produced;

incubating the said polymeric solid phase carrier with fluid to be measured selected from the group consisting of patient serum, cerebrospinal fluid (CSF), negative control serum and negative control CSF at approximately room temperature and for a predetermined period of time to thereby bind different types of specific immunoglobulins in said fluid to available binding sites on the said unpurified viral antigen(s);

again incubating said polymeric solid phase carrier with tagged anti-human specific immunoglobulin of the type wherein the specific immunoglobulin chosen is that desired to be measured, at approximately room temperature and for a predetermined period of time whereby a precise amount of said tagged anti-human specific immunoglobulin is bound to the specific immunoglobulin desired to be measured;

removing excess, unbound tagged anti-human specific immunoglobulin; and measuring the amount of bound tagged anti-human specific immunoglobulin to thereby quantify the amount of specific immunoglobulin, desired to be measured, in the patient serum.

2. The process of claim 1 which includes removing said fixing agent from said solid phase carrier prior to incubation with the fluid to be measured.

3. The process of claim 1 which includes blocking free binding sites on said solid phase carriers from binding to tagged anti-human specific immunoglobulin or other protein specific immunoglobulin.

4. The process of claim 1 wherein said solid phase carrier is a plastic ball having a diameter of between 4–8 mm.

5. The process of claim 4 wherein said plastic ball is made of polystyrene and is provided with a specular surface.

6. The process of claim 1 wherein the viral specific immunoglobulins to be measured are selected from the group consisting of IgG, IgM, IgE, IgA and IgD.

7. The process of claim 1 wherein said virus for infecting said cells is selected from the group consisting of measles virus and rubella virus.

8. In a kit for the assay of viral specific immunoglobulin having a plurality of testing cavities, a plurality of polymeric solid phase carriers, having a specular surface to which viral antigens are attached, having a diameter of between 4 millimeters and about 8 millimeters and having a density sufficient to be separated from a medium without centrifugation, standards, and a tagged anti-human specific immunoglobulin, the carriers, standards, and immunoglobulins being present in sufficient amounts to perform the assay, wherein the improvement comprises: the attachment of the viral antigen to said carrier by growing cells on said carrier which cells are infected with virus to produce said viral antigens which are used in an unpurified form.

* * * * *